US00PP29778P2

(12) United States Plant Patent
McCracken

(10) Patent No.: US PP29,778 P2
(45) Date of Patent: Oct. 30, 2018

(54) ***MAGNOLIA* PLANT NAMED 'STELLAR RUBY'**

(50) Latin Name: *Magnolia figo*
Varietal Denomination: Stellar Ruby

(71) Applicant: Thomas Patrick McCracken, Zebulon, NC (US)

(72) Inventor: Thomas Patrick McCracken, Zebulon, NC (US)

( * ) Notice: Subject to any disclaimer, the term of this patent is extended or adjusted under 35 U.S.C. 154(b) by 0 days.

(21) Appl. No.: 15/731,326

(22) Filed: May 25, 2017

(51) Int. Cl.
*A01H 5/00* (2018.01)

(52) U.S. Cl.
USPC ..... Plt./223

(58) Field of Classification Search
USPC ..... Plt./223
See application file for complete search history.

*Primary Examiner* — Susan Beth McCormick Ewoldt
(74) *Attorney, Agent, or Firm* — Penny J. Aguirre

(57) ABSTRACT

A new cultivar of *Magnolia* named 'Stellar Ruby' that is characterized by its a very narrow and dense pyramidal growth habit, its floriferous blooming habit, its flowers that are purple in color and fragrant, its fast plant growth habit, its cold hardiness at least to U.S.D.A. Zone 7, and its ability to bloom on plants that are young in age.

2 Drawing Sheets

Botanical classification: *Magnolia figo*.
Variety denomination: 'Stellar Ruby'.

BACKGROUND OF THE INVENTION

The present invention relates to a new and distinct cultivar of *Magnolia figo*. The new cultivar will be referred to hereafter by its cultivar name, 'Stellar Ruby'. 'Stellar Ruby' is a new cultivar of *Magnolia* grown for use as a landscape shrub.

The new cultivar of *Magnolia* is a selection from a controlled breeding program conducted by the Inventor in Zebulon, N.C. The objectives of the breeding program were to create a new *Magnolia* cultivar with fragrant purple flowers with good cold hardiness and evergreen foliage.

'Stellar Ruby' originated from a cross made in 2004 between an unnamed and unpatented plant of *Magnolia figo* var. *crassipes* as the female parent and an unnamed and unpatented plant of *Magnolia figo* var. *skinneriana* as the male parent. 'Stellar Ruby' was selected as a single unique plant in 2010 from amongst the resulting seedlings.

Asexual propagation of the new cultivar was first accomplished by semi-hardwood stem cuttings by the Inventor in Zebulon, N.C. in late spring of 2014. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Stellar Ruby' as a new and unique cultivar of *Magnolia*.

1. 'Stellar Ruby' exhibits a very narrow and dense pyramidal growth habit.
2. 'Stellar Ruby' exhibits a floriferous blooming habit.
3. 'Stellar Ruby' exhibits flowers that are purple in color and fragrant.

4. 'Stellar Ruby' exhibits a fast plant growth habit.
5. 'Stellar Ruby' exhibits very dark green foliage.
6. 'Stellar Ruby' exhibits cold hardiness at least to U.S.D.A. Zone 7.
7. 'Stellar Ruby' exhibits blooms on plants that are young in age.

The female parent of 'Stellar Ruby' differs from 'Stellar Ruby' in having flowers that are white in color, a spreading non pyramidal growth habit, flowers that have no fragrance and leaves that are pale green in color. The pollen parent of 'Stellar Ruby' differs from 'Stellar Ruby' in being less cold hardy and in having a low sprawling plant habit, flowers that are lighter purple in color and a less floriferous blooming habit. 'Stellar Ruby' can be most closely compared to the *Magnolia figo* var. *crassipes* cultivar 'Purple Queen' (not patented). 'Purple Queen' is similar to 'Stellar Ruby' in having flowers that are purple in color. 'Purple Queen' differs from 'Stellar Ruby' in being less cold hardy and in having flowers that are darker purple in color, a less floriferous blooming habit and a much more open growth habit.

BRIEF DESCRIPTION OF THE DRAWINGS

The accompanying colored photographs illustrate the overall appearance and distinct characteristics of the new *Magnolia*. The photographs were taken of a 2 year-old plant (from a cutting) as grown outdoors in a five-gallon container in Zebulon, N.C.

The photograph in FIG. 1 provides a side view of the plant habit of 'Stellar Ruby'.

Figure 1:
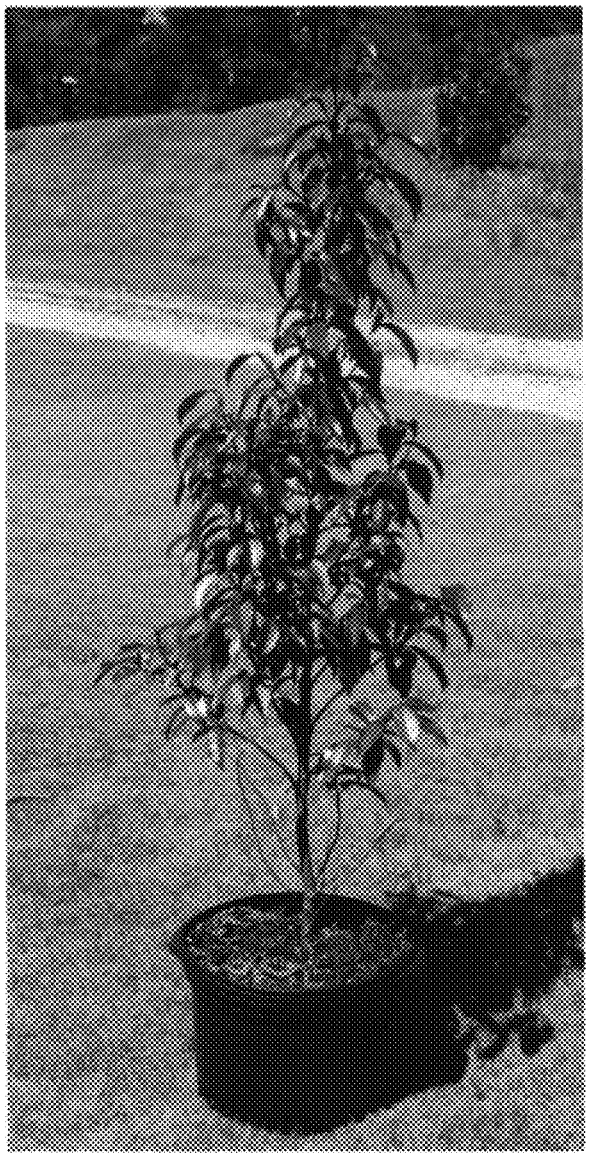
Figure 2:
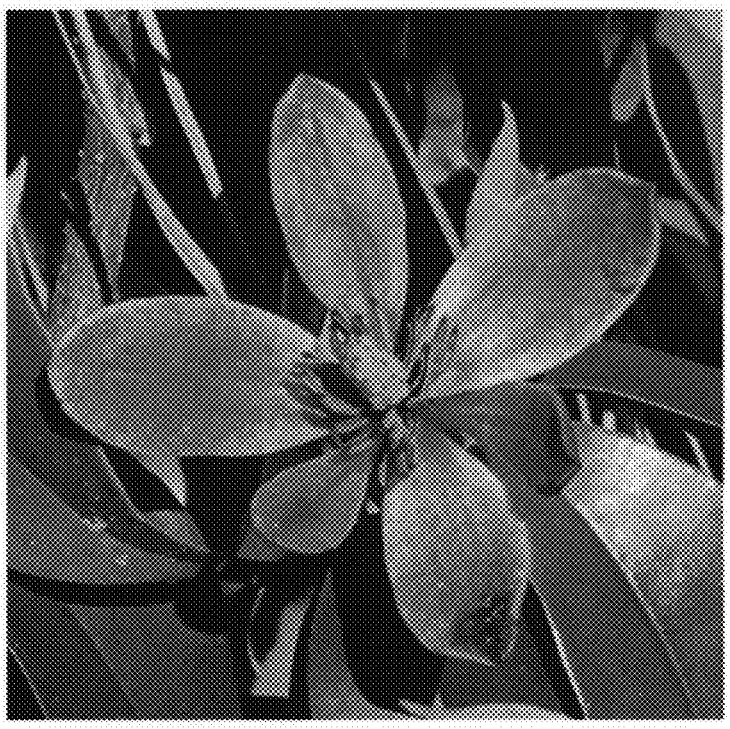

The photograph in FIG. 2 provides a close-up view of a flower of 'Stellar Ruby'.

Figure 3:
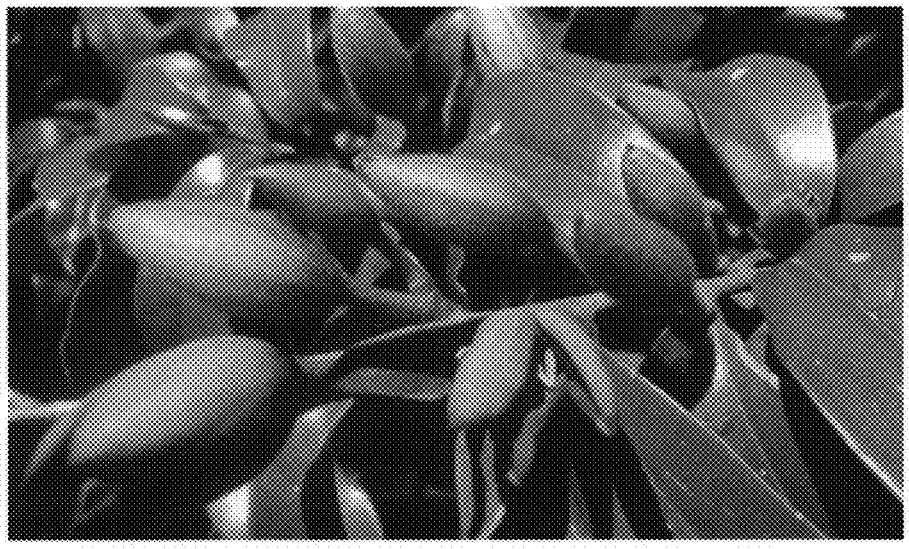

The photograph in FIG. 3 provides a close-up view of the flower buds of 'Stellar Ruby'.

The colors in the photographs are as close as possible with the photographic and printing technology utilized and the color values cited in the detailed botanical description accurately describe the colors of the new *Magnolia*.

DETAILED BOTANICAL DESCRIPTION

The following is a detailed description of 2 year-old plants of the new cultivar as grown outdoors in five-gallon containers in Zebulon, N.C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming habit.*—From early spring to early summer followed by sporadic blooms later in summer in Zebulon, N.C.

*Plant type.*—Evergreen tree (evergreen to −5° F. at short durations).

*Plant habit.*—Dense and narrowly pyramidal.

*Height and spread.*—An average of 4.6 m in height and 1.5 to 1.8 m in width as a 10 year-old plant in the landscape.

*Hardiness.*—At least in U.S.D.A. Zones 7 to 9.

*Diseases and pests.*—No resistance or susceptibility to diseases or pests has been observed.

*Propagation.*—Semi-hardwood stem cuttings.

*Growth rate.*—Moderate to vigorous.

*Root description.*—Fleshy with secondary roots fibrous, NN155A and maturing 158C in color.

*Root development.*—Roots very readily (much faster than plants of the parent species); fully roots in less than 2 months as a liner.

Branch description:

*Branch color.*—Young; 144A, mature; 165A with striations of 165B, trunk; 165A with striations of 165B.

*Branch surface.*—Young; pubescent, mature; finely barked with petiole scars and lenticels; about 5 per branch 2 cm in length, rounded, 165A in color, trunk; finely barked.

*Branching.*—An average of 25 lateral branches, an average of 6 secondary branches per lateral branch.

*Internode length.*—Average of 9 mm.

*Branch size.*—Trunk; an average of 5.5 cm at the soil line, lateral branches; an average of 30 cm in length and 4 mm in width, secondary branches; an average of 15 cm in length and 2.2 mm in width.

*Stipules.*—None observed.

Foliage description:

*Leaf type.*—Simple.

*Leaf shape.*—Elliptic.

*Leaf apex.*—Acuminate.

*Leaf base.*—Cuneate.

*Leaf arrangement.*—Alternate.

*Leaf venation.*—Pinnate, not conspicuous, color on upper surface; midrib 138A, others match leaf coloration, color lower surface; midrib 146D, others match leaf coloration.

*Leaf fragrance.*—None.

*Leaf color.*—Young upper and lower surface; 144C, mature upper surface; 147A (slightly darker), mature lower surface; 147B.

*Leaf number.*—An average of 10 per branch 14 cm in length.

*Leaf surface.*—Shiny and glabrous on upper surface and glabrous and dull on lower surface.

*Leaf substance.*—Thick.

*Petioles.*—An average of 5 mm in length and 2 mm in diameter, color 165A, surface pubescent, removal leaves petiole scar 165D in color and 2 mm in diameter.

Inflorescence description:

*Inflorescence type.*—Solitary from upper leaf axils.

*Flower number.*—An average of 3 to 5 per lateral branch (in different stages of opening).

*Flower fragrance.*—Strong, pleasant *Magnolia* fragrance.

*Flower longevity.*—An average of 4 to 5 days, depending on temperature.

*Flower type.*—Rotate.

*Flower size.*—An average of 6 cm in diameter and 2 cm in depth.

*Flower buds.*—Conical in shape, an average of 2.4 cm in length and 1.2 cm in width, a blend of 146C an 151B in color and flushed with N79C, pubescent surface.

*Petals.*—3 per flower, arranged in a single whorl, non-overlapping at base, narrowly elliptic in shape, an average of 2.5 cm in length and 9 mm in width, broadly acute apex, margins entire, base cuneate, aspect is primarily horizontal and slightly cupped, upper and lower surface is satiny, leathery substance, color upper surface when opening and fully open a blend of N79B and N79C, color lower surface when opening and fully open a blend of N79C and 161B.

*Sepals.*—3 per flower, petal-like, arranged in a single whorl, non-overlapping at base, elliptic in shape, an average of 3 cm in length and 1.3 cm in width, broadly acute to rounded apex, margins entire, base cuneate, aspect is primarily horizontal and slightly cupped, upper and lower surface is satiny, leathery substance, color upper surface when opening and fully open a blend of N79B and N79C, color lower surface when opening and fully open a blend of N79C and 161B.

*Peduncles.*—Slightly oval in shape, average of 1.7 cm in length and 2.5 mm in diameter, 165A in color with wooly pubescent surface.

Reproductive organs:

*Gynoecium.*—Numerous carpels (average of 36) spirally arranged forming a conical structure (pineapple-like) 1.2 cm in length and 3.5 mm in width, stigmas and styles (not distinguishable from each other); triangular, N79A in color, and an average of 1 mm in length, ovaries; broadly lanceolate in shape, 2 mm in length and 160C in color.

*Androecium.*—An average of 28 stamens, filaments are 2 mm in length and N186B in color, anthers; linear in shape, an average of 7 mm in length and 1 mm in width, 161B with 2 vertical stripe of N79A in color, pollen is abundant and 155A in color.

*Fruit and seed.*—Not observed to date.

It is claimed:

1. A new and distinct cultivar of *Magnolia* plant named 'Stellar Ruby' as herein illustrated and described.

* * * * *